United States Patent
Errico et al.

(10) Patent No.: US 8,858,564 B2
(45) Date of Patent: *Oct. 14, 2014

(54) WEDGE PLATE INSERTER/IMPACTOR AND RELATED METHODS FOR USE IN IMPLANTING AN ARTIFICIAL INTERVERTEBRAL DISC

(75) Inventors: Joseph P. Errico, Green Brook, NJ (US); Michael W. Dudasik, Nutley, NJ (US); Rafail Zubok, Midland Park, NJ (US)

(73) Assignee: SpineCore, Inc., Allendale, NJ (US)

( * ) Notice: Subject to any disclaimer, the term of this patent is extended or adjusted under 35 U.S.C. 154(b) by 1125 days.

This patent is subject to a terminal disclaimer.

(21) Appl. No.: 10/784,645
(22) Filed: Feb. 23, 2004
(65) Prior Publication Data
US 2006/0052780 A1    Mar. 9, 2006

Related U.S. Application Data (63) Continuation of application No. 10/425,267, filed on Apr. 29, 2003, now Pat. No. 7,235,081, which is a
(Continued)

(51) Int. Cl.
A61B 17/56 (2006.01)
A61B 17/70 (2006.01)
(Continued)

(52) U.S. Cl.
CPC ........ *A61F 2/442* (2013.01); *A61B 2017/0256* (2013.01); *A61F 2002/4628* (2013.01);
(Continued)

(58) Field of Classification Search
CPC ............... A61F 2/4611; A61F 2/4684; A61F 2002/30772; A61F 2002/30518; A61F 2250/0006

USPC ............ 606/99, 79–81, 91, 100, 1, 204, 206, 606/217, 86 A, 101, 104, 246, 914, 53
See application file for complete search history.

(56) References Cited

U.S. PATENT DOCUMENTS

| 801,151 A | 10/1905 | McKeever et al. |
| 856,660 A | 6/1907 | Schall et al. |

(Continued)

FOREIGN PATENT DOCUMENTS

WO    02/071986 A2    9/2002

*Primary Examiner* — Brian Pellegrino
(74) *Attorney, Agent, or Firm* — Lerner, David, Littenberg, Krumholz & Mentlik, LLP (57) ABSTRACT

A wedge plate inserter/impactor instrument is provided primarily for holding, inserting, repositioning, removing, impacting, extracting, and otherwise manipulating an artificial intervertebral disc having features suitable for being manipulated thereby. A spring-loaded holding pin of the instrument can be used to engage a corresponding hole on the disc and confront the angled surfaces of the disc to enable the holding and manipulation of the disc. A forward wedge extension of the inserter/impactor has upper and lower surfaces that engage inwardly facing surfaces of the disc to hold the baseplates of the disc at a preferred lordosis angle with respect to one another. The instrument can engage the disc from a variety of surgical approach angles.

4 Claims, 5 Drawing Sheets

Related U.S. Application Data continuation-in-part of application No. 10/282,356, filed on Oct. 29, 2002, now Pat. No. 7,169,182, which is a continuation-in-part of application No. 10/256,160, filed on Sep. 26, 2002, now Pat. No. 6,898,032, which is a continuation-in-part of application No. 10/175,417, filed on Jun. 19, 2002, now Pat. No. 7,563,285, which is a continuation-in-part of application No. 10/151,280, filed on May 20, 2002, now Pat. No. 7,604,664, which is a continuation-in-part of application No. 09/970,479, filed on Oct. 4, 2001, now Pat. No. 6,669,730, and a continuation-in-part of application No. 10/140,153, filed on May 7, 2002, now abandoned, said application No. 09/970,479 is a continuation-in-part of application No. 09/968,046, filed on Oct. 1, 2001, now abandoned, said application No. 10/140,153 is a continuation-in-part of application No. 09/970,479, and a continuation-in-part of application No. 10/128,619, filed on Apr. 23, 2002, now Pat. No. 6,863,689, which is a continuation-in-part of application No. 09/906,119, filed on Jul. 16, 2001, now Pat. No. 6,607,559, and a continuation-in-part of application No. 09/982,148, filed on Oct. 18, 2001, now Pat. No. 6,673,113.

(51) Int. Cl.
*A61F 2/44* (2006.01)
*A61B 17/02* (2006.01)
*A61F 2/46* (2006.01)
*A61F 2/30* (2006.01)

(52) U.S. Cl.
CPC .. *A61F 2002/30571* (2013.01); *A61F 2/30742* (2013.01); *A61F 2002/30594* (2013.01); *A61F 2230/005* (2013.01); *A61F 2220/0033* (2013.01); *A61F 2002/30507* (2013.01); *A61F 2002/302* (2013.01); *A61F 2002/30662* (2013.01); *A61F 2310/00017* (2013.01); *A61F 2002/30565* (2013.01); *A61F 2002/30772* (2013.01); *A61F 2310/00023* (2013.01); *A61F 2002/30378* (2013.01); *A61F 2/4611* (2013.01); *A61F 2002/30769* (2013.01); *A61F 2002/30171* (2013.01); *A61F 2002/30443* (2013.01); *A61F 2310/00365* (2013.01); *A61F 2002/30616* (2013.01); *A61F 2220/0025* (2013.01); *A61F 2002/30502* (2013.01); *A61F 2/446* (2013.01); *A61F 2002/443* (2013.01); *A61F 2002/30604* (2013.01); *A61F 2002/30365* (2013.01); *A61F 2002/30841* (2013.01); *A61F 2002/30538* (2013.01); *A61F 2230/0034* (2013.01); *A61F 2002/4619* (2013.01); *A61F 2250/0006* (2013.01); *A61F 2002/30446* (2013.01); *A61F 2002/30774* (2013.01); *A61F 2220/0058* (2013.01); *A61F 2002/30454* (2013.01); *A61F 2002/30444* (2013.01); *A61F 2002/30187* (2013.01); *A61F 2220/0041* (2013.01); *A61F 2002/30563* (2013.01); *A61F 2002/30433* (2013.01); *A61F 2002/30785* (2013.01); *A61F 2/4425* (2013.01); *A61F 2002/30649* (2013.01); *A61F 2/4684* (2013.01); *A61F 2002/30528* (2013.01); *A61F 2002/30909* (2013.01); *A61F 2002/30492* (2013.01); *A61F 2002/30331* (2013.01); *A61F 2002/4627* (2013.01); *A61F 2230/0065* (2013.01); *A61F 2002/30518* (2013.01); *A61F 2002/30441* (2013.01); *A61F 2002/30451* (2013.01); *A61F 2/30767* (2013.01); *A61F 2002/3092* (2013.01); *A61F 2002/30975* (2013.01)
USPC .......................................... 606/99; 606/86 A (56) References Cited

U.S. PATENT DOCUMENTS

| | | |
|---|---|---|
| 1,099,811 A | 6/1914 | Moise et al. |
| 1,117,562 A | 11/1914 | Hale |
| 1,243,860 A | 10/1917 | Olson et al. |
| 1,425,845 A | 8/1922 | Foster |
| 1,539,221 A | 5/1925 | Tennant |
| 1,882,462 A | 10/1932 | Weber |
| 2,121,682 A | 6/1938 | Boucher |
| 2,546,287 A | 3/1951 | Zelgert |
| 3,195,380 A | 7/1965 | Bicks |
| 3,326,254 A | 6/1967 | Diehl |
| 3,867,728 A | 2/1975 | Stubstad et al. |
| 4,309,777 A | 1/1982 | Patil |
| 4,605,417 A | 8/1986 | Fleischauer |
| 4,759,766 A | 7/1988 | Buettner-Janz et al. |
| 4,759,769 A | 7/1988 | Hedman et al. |
| 4,820,305 A | 4/1989 | Harms et al. |
| 4,932,969 A | 6/1990 | Frey et al. |
| 4,968,010 A | 11/1990 | Odobasic |
| 4,997,432 A | 3/1991 | Keller |
| 5,015,247 A | 5/1991 | Michelson |
| 5,026,373 A | 6/1991 | Ray et al. |
| 5,236,460 A | 8/1993 | Barber |
| 5,314,477 A | 5/1994 | Marnay |
| 5,370,697 A | 12/1994 | Baumgartner |
| 5,401,269 A | 3/1995 | Buttner-Janz et al. |
| 5,425,773 A | 6/1995 | Boyd et al. |
| 5,507,816 A | 4/1996 | Bullivant |
| 5,556,431 A | 9/1996 | Buttner-Janz |
| 5,562,738 A | 10/1996 | Boyd et al. |
| 5,658,337 A | 8/1997 | Kohrs et al. |
| 5,676,701 A | 10/1997 | Yuan et al. |
| 5,683,399 A | 11/1997 | Jones |
| 5,683,465 A | 11/1997 | Shinn et al. |
| 5,749,916 A | 5/1998 | Richelsoph |
| 5,755,798 A | 5/1998 | Papavero et al. |
| 5,766,252 A | 6/1998 | Henry et al. |
| 5,782,832 A | 7/1998 | Larsen et al. |
| 5,893,889 A | 4/1999 | Harrington |
| 5,895,428 A | 4/1999 | Berry |
| 5,899,941 A | 5/1999 | Nishijima et al. |
| 5,989,291 A | 11/1999 | Ralph et al. |
| 6,015,436 A | 1/2000 | Schonhoffer |
| 6,039,763 A | 3/2000 | Shelokov |
| 6,159,211 A | 12/2000 | Boriani et al. |
| 6,228,023 B1 * | 5/2001 | Zaslavsky et al. ............... 606/1 |
| 6,368,350 B1 | 4/2002 | Erickson et al. |
| 6,375,682 B1 | 4/2002 | Fleischmann et al. |
| 6,391,058 B1 | 5/2002 | Kuslich et al. |
| 6,402,785 B1 | 6/2002 | Zdeblick et al. |
| 6,440,133 B1 | 8/2002 | Beale et al. |
| 6,471,725 B1 | 10/2002 | Ralph et al. |
| 6,514,256 B2 | 2/2003 | Zucherman et al. |
| 6,517,580 B1 | 2/2003 | Ramadan et al. |
| 6,527,786 B1 * | 3/2003 | Davis et al. ................... 606/151 |
| 6,558,387 B2 | 5/2003 | Errico et al. |
| 6,582,431 B1 | 6/2003 | Ray |
| 6,582,451 B1 | 6/2003 | Marucci et al. |
| 6,582,468 B1 | 6/2003 | Gauchet |
| 6,599,291 B1 | 7/2003 | Foley et al. |
| 6,610,092 B2 | 8/2003 | Ralph et al. |
| 6,645,249 B2 | 11/2003 | Ralph et al. |
| 6,673,113 B2 | 1/2004 | Ralph et al. |
| 6,682,562 B1 | 1/2004 | Viart et al. |
| 6,706,068 B2 | 3/2004 | Ferree |
| 6,712,819 B2 | 3/2004 | Zucherman et al. |
| 6,733,532 B1 | 5/2004 | Gauchet et al. |
| 6,755,841 B2 * | 6/2004 | Fraser et al. ..................... 606/99 |
| 6,887,274 B2 | 5/2005 | Ralph et al. |

(56) References Cited

U.S. PATENT DOCUMENTS

| | | | |
|---|---|---|---|
| 6,989,032 B2 | 1/2006 | Errico et al. |
| 7,011,684 B2 | 3/2006 | Eckman |
| 7,025,787 B2 | 4/2006 | Bryan et al. |
| 7,048,764 B2 | 5/2006 | Ferree |
| 7,060,099 B2 | 6/2006 | Carli et al. |
| 7,066,959 B2 | 6/2006 | Errico et al. |
| 7,083,651 B2 | 8/2006 | Diaz et al. |
| 7,115,132 B2 * | 10/2006 | Errico et al. ............. 606/61 |
| 7,160,327 B2 | 1/2007 | Errico et al. |
| 7,169,182 B2 | 1/2007 | Errico et al. |
| 7,214,244 B2 | 5/2007 | Zubok et al. |
| 7,235,081 B2 | 6/2007 | Errico et al. |
| 7,235,082 B2 | 6/2007 | Bartish et al. |
| 7,326,216 B2 | 2/2008 | Bertagnoli et al. |
| 7,326,250 B2 | 2/2008 | Beaurain et al. |
| 7,491,241 B2 | 2/2009 | Errico et al. |
| 7,575,576 B2 | 8/2009 | Zubok et al. |
| 7,635,368 B2 | 12/2009 | Errico et al. |
| 7,713,302 B2 | 5/2010 | Ralph et al. |
| 2001/0016773 A1 | 8/2001 | Serhan et al. |
| 2001/0039452 A1 | 11/2001 | Zucherman et al. |
| 2002/0082597 A1 | 6/2002 | Fraser |
| 2002/0111681 A1 | 8/2002 | Ralph et al. |
| 2002/0111682 A1 | 8/2002 | Ralph et al. |
| 2002/0111683 A1 | 8/2002 | Ralph et al. |
| 2002/0111684 A1 | 8/2002 | Ralph et al. |
| 2002/0111685 A1 | 8/2002 | Ralph et al. |
| 2002/0128714 A1 | 9/2002 | Manasas et al. |
| 2002/0193880 A1 | 12/2002 | Fraser |
| 2003/0009223 A1 | 1/2003 | Fehling et al. |
| 2003/0009224 A1 | 1/2003 | Kuras |
| 2003/0014110 A1 | 1/2003 | Ralph et al. |
| 2003/0014111 A1 | 1/2003 | Ralph et al. |
| 2003/0014112 A1 | 1/2003 | Ralph et al. |
| 2003/0023306 A1 | 1/2003 | Liu et al. |
| 2003/0028249 A1 | 2/2003 | Baccelli et al. |
| 2003/0040801 A1 | 2/2003 | Ralph et al. |
| 2003/0045939 A1 | 3/2003 | Casutt |
| 2003/0055503 A1 | 3/2003 | O'Neil |
| 2003/0060886 A1 | 3/2003 | Van Hoeck et al. |
| 2003/0069586 A1 | 4/2003 | Errico et al. |
| 2003/0069642 A1 | 4/2003 | Ralph et al. |
| 2003/0074067 A1 | 4/2003 | Errico et al. |
| 2003/0078662 A1 | 4/2003 | Ralph et al. |
| 2003/0078666 A1 | 4/2003 | Ralph et al. |
| 2003/0078667 A1 | 4/2003 | Manasas et al. |
| 2003/0083749 A1 | 5/2003 | Kuslich et al. |
| 2003/0100951 A1 | 5/2003 | Serhan et al. |
| 2003/0135278 A1 | 7/2003 | Eckman |
| 2003/0149482 A1 | 8/2003 | Michelson |
| 2003/0187508 A1 | 10/2003 | Cauthen |
| 2003/0191533 A1 | 10/2003 | Dixon et al. |
| 2003/0191534 A1 | 10/2003 | Viart et al. |
| 2003/0204260 A1 | 10/2003 | Ferree |
| 2003/0208271 A1 | 11/2003 | Kuras |
| 2003/0208273 A1 | 11/2003 | Eisermann et al. |
| 2003/0229358 A1 | 12/2003 | Errico et al. |
| 2003/0233097 A1 | 12/2003 | Ferree |
| 2003/0233148 A1 | 12/2003 | Ferree |
| 2004/0002759 A1 | 1/2004 | Ferree |
| 2004/0002762 A1 | 1/2004 | Hawkins |
| 2004/0010316 A1 | 1/2004 | William et al. |
| 2004/0030389 A1 | 2/2004 | Ferree |
| 2004/0030390 A1 | 2/2004 | Ferree |
| 2004/0034426 A1 | 2/2004 | Errico et al. |
| 2004/0059343 A1 * | 3/2004 | Shearer et al. ............. 606/107 |
| 2004/0267276 A1 | 12/2004 | Camino et al. |
| 2005/0119665 A1 * | 6/2005 | Keller ............. 606/99 |
| 2005/0131542 A1 | 6/2005 | Benzel et al. |
| 2005/0177171 A1 | 8/2005 | Wetzler et al. |
| 2007/0016221 A1 | 1/2007 | Beyersdorff et al. |
| 2007/0198092 A1 | 8/2007 | Errico et al. |

* cited by examiner

FIG. 1G

FIG. 1H
(SECTION C-C ON FIG. 1I)

FIG. 1I

FIG. 1J
(PERSPECTIVE OF FIG. 1H)

FIG. 1K
(SECTION A-A ON FIG. 1G)

FIG. 1L
(SECTION B-B ON FIG. 1G)

FIG. 4E ial Intervertebral Disc", now U.S. Pat. No. 7,169,182 ("the

WEDGE PLATE INSERTER/IMPACTOR AND RELATED METHODS FOR USE IN IMPLANTING AN ARTIFICIAL INTERVERTEBRAL DISC

CROSS-REFERENCE TO RELATED APPLICATIONS

The present application is a continuation application of U.S. patent application Ser. No. 10/425,267 (filed Apr. 29, 2003) entitled "Wedge Plate Inserter/Impactor and Related Methods for use in Implanting an Artificial Intervertebral Disc", now U.S. Pat. No. 7,235,081 ("the '081 patent"), which is a continuation-in-part application of U.S. patent application Ser. No. 10/282,356 (filed Oct. 29, 2002) entitled "Instrumentation and Methods For Use In Implanting an Artificial Intervertebral Disc", now U.S. Pat. No. 7,169,182 ("the '182 patent"), which is a continuation-in-part application of U.S. patent application Ser. No. 10/256,160 (filed Sep. 26, 2002) entitled "Artificial Intervertebral Disc Having Limited Rotation Using a Captured Ball and Socket Joint With a Solid Ball and Compression Locking Post", now U.S. Pat. No. 6,989,032 ("the '032 patent"), which is a continuation-in-part application of U.S. patent application Ser. No. 10/175,417 (filed Jun. 19, 2002) entitled "Artificial Intervertebral Disc Utilizing a Ball Joint Coupling", which is a continuation-in-part application of U.S. patent application Ser. No. 10/151,280 (filed May 20, 2002) entitled "Tension Bearing Artificial Disc Providing a Centroid of Motion Centrally Located Within an Intervertebral Space", which is a continuation-in-part application of U.S. patent application Ser. No. 09/970,479 (filed Oct. 4, 2001) entitled "Intervertebral Spacer Device Utilizing a Spirally Slotted Belleville Washer Having Radially Extending Grooves", now U.S. Pat. No. 6,669,730 ("the '730 patent"), and U.S. patent application Ser. No. 10/151,280 is a continuation-in-part application of U.S. patent application Ser. No. 10/140,153 (filed May 7, 2002) entitled "Artificial Intervertebral Disc Having a Flexible Wire Mesh Vertebral Body Contact Element", now abandoned, and U.S. patent application Ser. No. 09/970,479 (as detailed above) is a continuation-in-part application of U.S. patent application Ser. No. 09/968,046 (filed Oct. 1, 2001) entitled "Inte'rvertebral Spacer Device Utilizing a Belleville Washer Having Radially Extending Grooves", now abandoned and U.S. patent application Ser. No. 10/140,153 (detailed above) is a continuation-in-part application of both U.S. patent application Ser. No. 09/970,479 (detailed above) as well as U.S. patent application Ser. No. 10/128,619 (filed Apr. 23, 2002) entitled "Intervertebral Spacer Having a Flexible Wire Mesh Vertebral Body Contact Element", now U.S. Pat. No. 6,863,689 ("the '689 patent"), which is a continuation-in-part application of U.S. patent application Ser. No. 09/906,119 (filed Jul. 16, 2001) and entitled "Trial Intervertebral Distraction Spacers", now U.S. Pat. No. 6,607,559 ("the '559 patent"), and U.S. patent application Ser. No. 10/128,619 (as detailed above) is a continuation-in-part of U.S. patent application Ser. No. 09/982,148 (filed Oct. 18, 2001) and entitled "Intervertebral Spacer Device Having Arch Shaped Spring Elements", now U.S. Pat. No. 6,673,113 ("the '113 patent"). All of the above mentioned applications are hereby incorporated by reference herein in their respective entireties.

FIELD OF THE INVENTION

This invention relates generally to systems and methods for use in spine arthroplasty, and more specifically to instruments for inserting and impacting artificial intervertebral discs, and methods of use thereof.

BACKGROUND OF THE INVENTION

The bones and connective tissue of an adult human spinal column consists of more than twenty discrete bones coupled sequentially to one another by a tri-joint complex that consists of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. With respect to the failure of the intervertebral disc, and the insertion of implants and/or height restorative devices, several methods and devices have been disclosed in the prior art that achieve immobilization and/or fusion of adjacent bones by implanting artificial assemblies in or on the spinal column. More recently, the development of non-fusion implant devices, which purport to permit continued natural movement in the tri-joint complex, have provided great promise as a preferably alternative to fusion devices. The region of the back that needs to be corrected, as well as the individual variations in anatomy, determine the appropriate surgical protocol and implantation assembly. Generally, the preparation of the intervertebral space for the receipt of fusion or non-fusion devices involves removing the damaged disc material and thereafter distracting the adjacent vertebral bones to their appropriate distance apart. Once the proper height of the intervertebral space is restored, the fusion or non-fusion device can be implanted.

It is an object of the invention to provide instrumentation and methods that enable surgeons to more accurately, easily, and efficiently implant fusion or non-fusion devices. Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which includes, among other aspects, an inserter/impactor (sometimes referred to herein as an "inserter/impactor") useful for holding and manipulating artificial intervertebral discs.

More particularly, the systems and methods disclosed herein are intended for use in spine arthroplasty procedures, and specifically for use with the systems and methods described herein in conjunction with the systems and methods in conjunction with the systems and methods described in U.S. patent application Ser. No. 10/282,356 (filed Oct. 29, 2002) entitled "Instrumentation and Methods For Use In Implanting an Artificial Intervertebral Disc" (hereinafter referred to as "the '356 application") as well as U.S. patent application Ser. No. 10/256,160 (filed Sep. 26, 2002) entitled "Artificial Intervertebral Disc Having Limited Rotation Using a Captured Ball and Socket Joint With a Solid Ball and Compression Locking Post" (hereinafter referred to as "the '160 application") as well as U.S. patent application Ser. No. 09/906,127 (filed Jul. 16, 2001) entitled "Insertion Tool For Use With Intervertebral Spacers" (hereinafter referred to as "the '127 application"), both applications of which are mentioned above. However, it should be understood that the systems and methods described herein are also suitable for use with other systems and methods without departing from the scope of the invention.

While the instrumentation described herein (e.g., the inserter/impactor) will be discussed for use with the artificial intervertebral disc of FIGS. 1g-n of the '356 application (hereinafter, such figures will merely be referred to as "FIGS. 1g-n"), such discussions are merely by way of example and not intended to be limiting of their uses. Thus, it should be understood that the instrumentation and methods can be used with any of the artificial intervertebral discs disclosed in the '356 or '160 applications, or any other artificial intervertebral disc having (or being modifiable or modified to have) suitable features therefor. Moreover, it is anticipated that the features of the artificial intervertebral discs (e.g., plate surfaces and engagement holes) that are used by the inserter/impactor discussed herein to hold and/or manipulate the artificial intervertebral disc can be applied, individually, or collectively or in various combinations, to other trials, spacers, artificial intervertebral discs, or other orthopedic devices as stand-alone innovative features for enabling such trials, spacers, artificial intervertebral discs, or other orthopedic devices to be more efficiently and more effectively held and/or manipulated by the inserter/impactor described herein or by tools having suitable features. In addition, it should be understood that the invention encompasses instrumentation and methods for implanting artificial intervertebral discs, spacers, trials (static or dynamic), and/or other orthopedic devices, that have one or more of the features disclosed herein, in any combination, and that the invention is therefore not limited to artificial intervertebral discs, spacers, trials, and/or other orthopedic devices having all of the features simultaneously.

Preferably, with regards to each artificial intervertebral disc to be implanted, a plurality of sizes of the artificial intervertebral disc would be available (e.g., the artificial intervertebral disc 160 of FIGS. 1g-n). That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. It should be understood that the artificial intervertebral discs can be offered in a variety of dimensions without departing from the scope of the invention, and that the dimensions specifically identified and quantified herein are merely exemplary. Each of the plurality of artificial intervertebral disc preferably further includes features that can be used by the inserter/impactor (described below) and/or the inserter/impactor described in the '356 application.

With regard to features that can be used by the inserter/impactor described in the '356 application, each artificial intervertebral disc includes an anteriorly facing flat surface, flanked by two anteriolaterally facing flat surfaces (one on each side of the anteriorly facing flat surface), and, to provide for holding of the disc for an anterior insertion approach, a hole spaced from the anteriorly facing flat surface, the hole having a longitudinal axis parallel to the anteriorly facing flat surface. The holding pin of the inserter/impactor fits within the hole, and the angled flat surfaces of the disc fit against the correspondingly angled flat surfaces of the inserter/impactor, and operation of the inserter/impactor pulls the holding pin toward the flat surface of the inserter/impactor opposite the pin, to rigidly hold the disc by the lower baseplate. The holding pin protrudes from the wedge-shaped extended surface of the distal end of the inserter/impactor and is restricted from upward movement with respect to the distal head by the presence of the wedge-shaped extended surface of the distal end of the inserter/impactor. More particularly, with any attempted upward movement of the holding pin, the pin encounters the upper surface of the channel in which the pin travels, preventing any such upward movement. When the intervertebral disc is held in this manner, rotation of the disc about a longitudinal axis relative to the inserter/impactor is prevented by interference of the corners of the disc's flat surfaces and the corners of the inserter/impactor's flat surfaces, similar to the manner in which a wrench holding a nut prevents rotation of the nut relative to the wrench. Further, when the disc is held in this manner, rotation of the disc about a lateral axis of the disc relative to the inserter/impactor is prevented by interference of the inwardly facing surface of the first baseplate (e.g., upper baseplate) of the disc and the corresponding surface (e.g., upper surface) of the wedge on the distal end, and by interference of the inwardly facing surface of the second baseplate (e.g., lower baseplate) of the disc and the correspoding surface (e.g., lower surface) of the wedge on the distal end. It is preferable that the wedge on the inserter/impactor will interfere between the first and second baseplates (e.g., upper and lower) so that the surfaces of the first and second baseplates align at a preferred 15 degrees angle of lordosis when the disc is held by the inserter/impactor.

Preferably, in order to provide for a holding of the disc for two additional (here, anteriolateral) insertion approaches, each disc also include two additional holes, one spaced apart from one of the anteriolaterally facing flat surfaces, and the other spaced apart from the other of the anteriolaterally facing flat surfaces. Accordingly, operation of the inserter/impactor can fit the holding pin into either of these two additional holes, and hold the anteriolaterally facing flat surface (the one associated with the hole into which the pin is fit) of the disc against the flat surface of the inserter/impactor opposite the pin. It should be understood that preferably, in order to facilitate these two additional approaches, the angle separating the anteriorly facing flat surface of the disc and one of the anteriolaterally facing flat surfaces of the disc is equal to the angle separating the anteriorly facing flat surface and the other of the anteriolaterally facing flat surfaces.

BRIEF DESCRIPTION OF THE DRAWINGS

FIGS. 2a-d show side (FIG. 2a), perspective (FIG. 2b), and close-up perspective (FIG. 2c) views of a wedge plate inserter/impactor of the present invention, including a partial cross-section view of a knob coupled to a shaft of the wedge plate inserter/impactor.

DETAILED DESCRIPTION OF THE PREFERRED EMBODIMENTS

While the invention will be described more fully hereinafter with reference to the accompanying drawings, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

A preferred embodiment of an artificial intervertebral disc (e.g., artificial intervertebral disc 160) for use with the instrumentation of the present invention is referenced and described in the '356 application, and the same description is hereby incorporated by reference herein. The artificial intervertebral disc illustrated in FIGS. 1g-n of the '356 application is discussed herein with reference to such figures, as an example of an artificial intervertebral disc suitable for use with the present invention.

A preferred embodiment of a wedge plate inserter/impactor of the present invention will now be described.

Figure 1G:
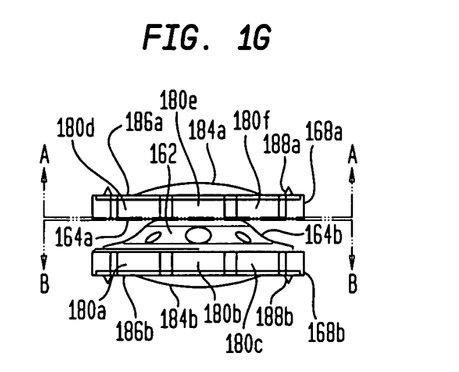
FIGS. 1g-n of the '356 application show front (FIG. 1g), side cutaway (FIG. 1h), top (FIG. 1i), perspective cutaway (FIG. 1j), bottom cutaway (FIG. 1k), top cutaway (FIG. 1l), bottom perspective (FIG. 1m), and top perspective (FIG. 1n) views of an exemplary artificial intervertebral disc for use with the present invention.
Figure 1H:
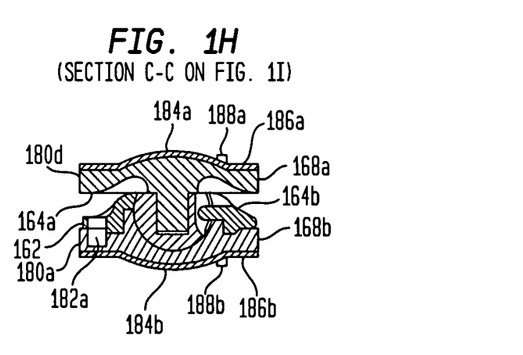
Figure 1I:
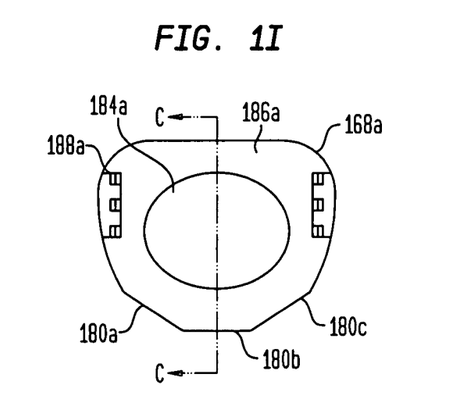
Figure 1J:
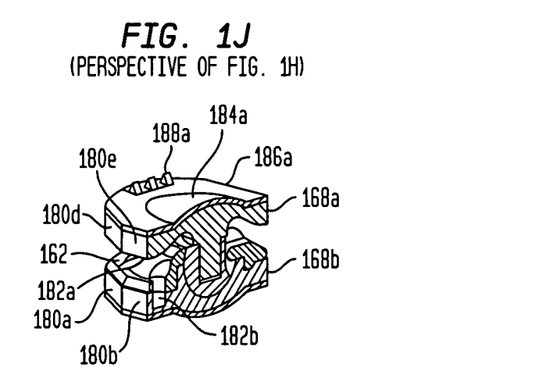
Figure 1K:
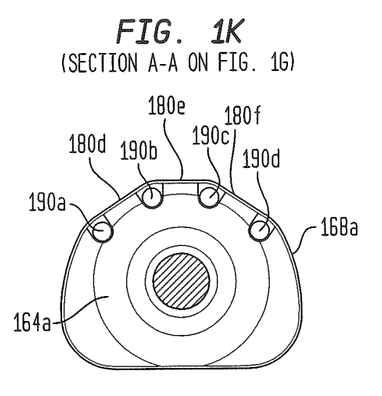
Figure 1L:
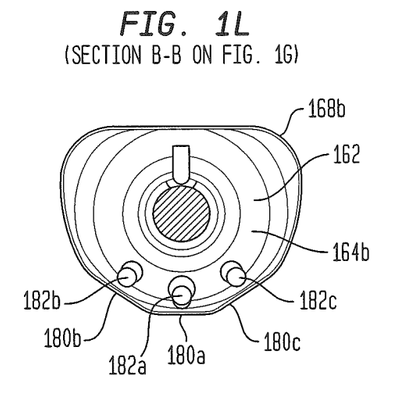
Figure 1M:
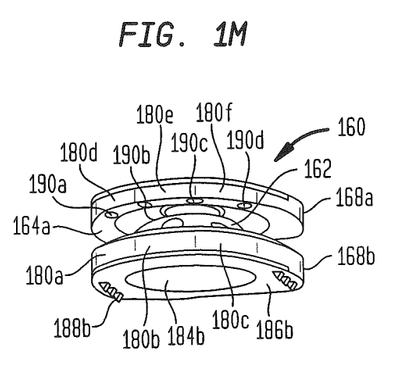
Figure 1N:
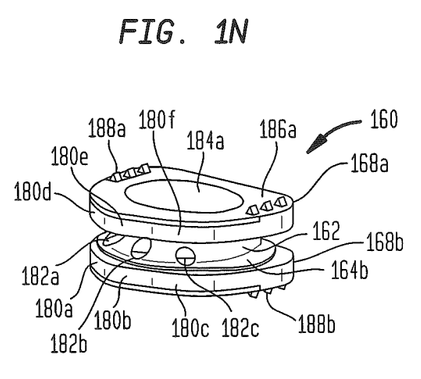
Figure 2A:
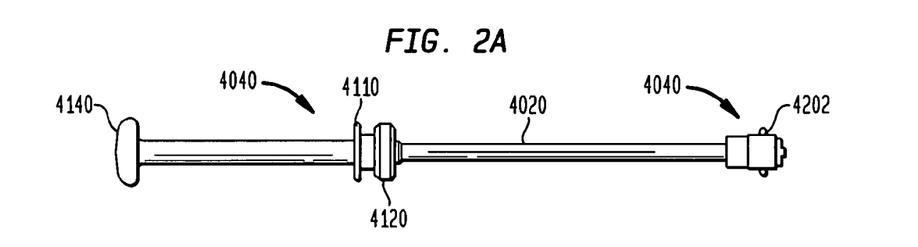
Figure 2B:
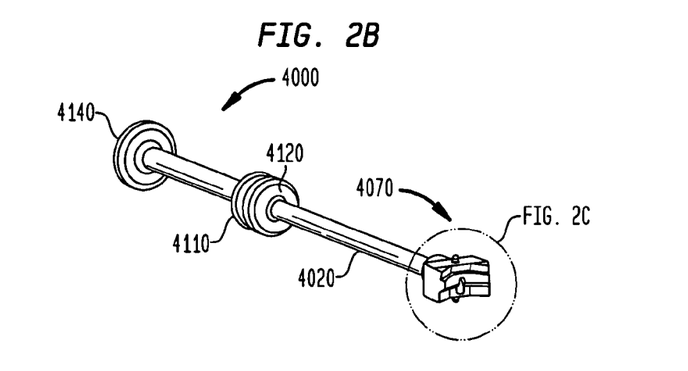
Figures 2C, 2D:
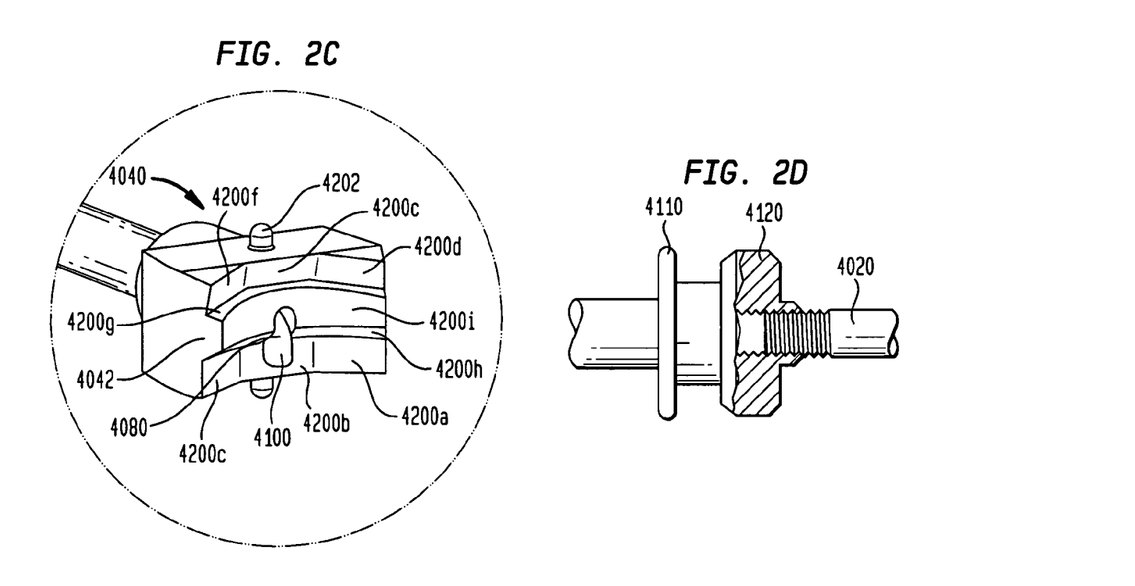
Figure 3A:
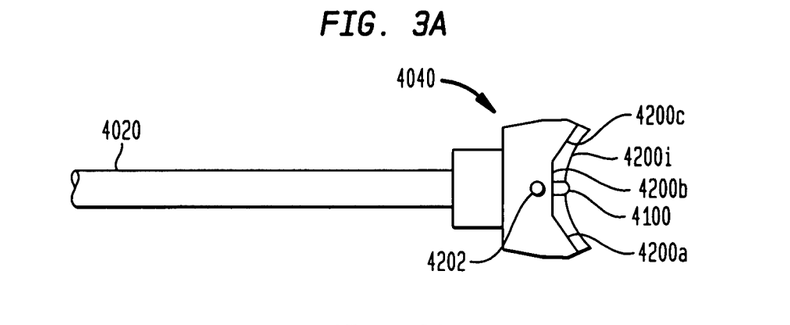
FIGS. 3a-d show bottom (FIG. 3a), side (FIG. 3b), top (FIG. 3c), and side cutaway (FIG. 3d) views of a distal end of a wedge plate inserter/impactor of the present invention.
Figure 3B:
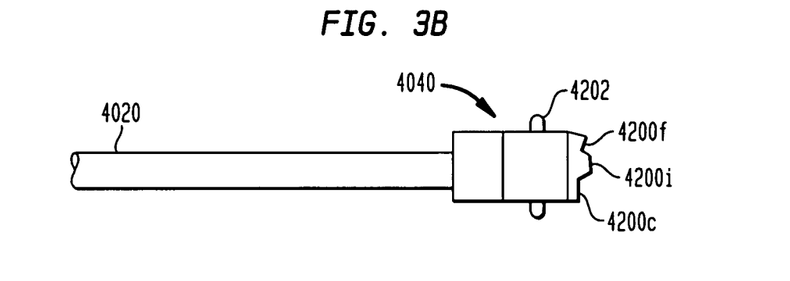
Figure 3C:
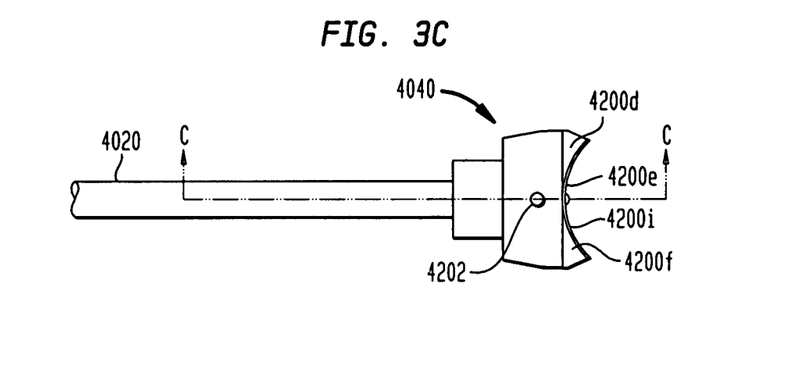
Figure 3D:
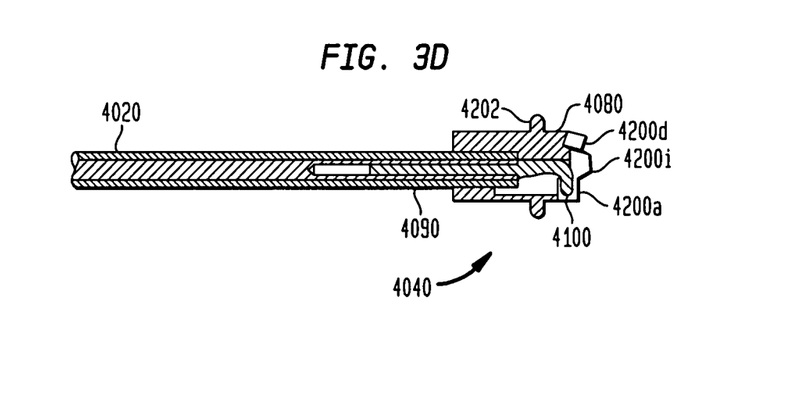
Figure 4A:
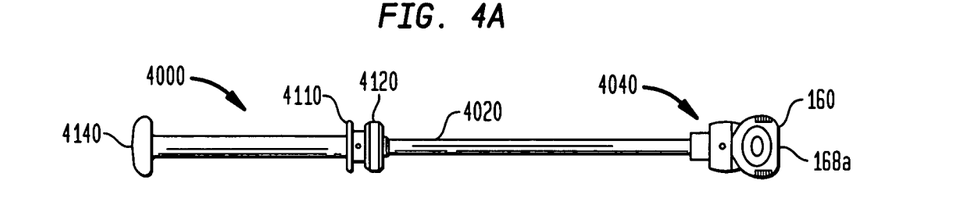
FIGS. 4a-b show top (FIG. 4a) and side (FIG. 4b) views of a wedge plate inserter/impactor of the present invention holding an exemplary artificial intervertebral disc.
Figure 4B:
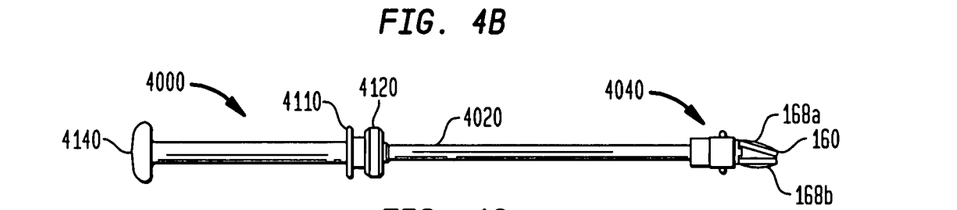
Figure 4C:
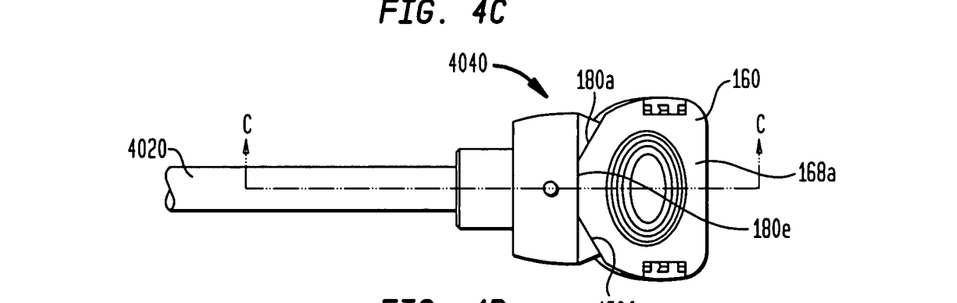
FIGS. 4c-e show top (FIG. 4c), side (FIG. 4d), and side cutaway (FIG. 4e) views of a distal end of a wedge plate inserter/impactor of the present invention holding an exemplary artificial intervertebral disc.
Figure 4D:
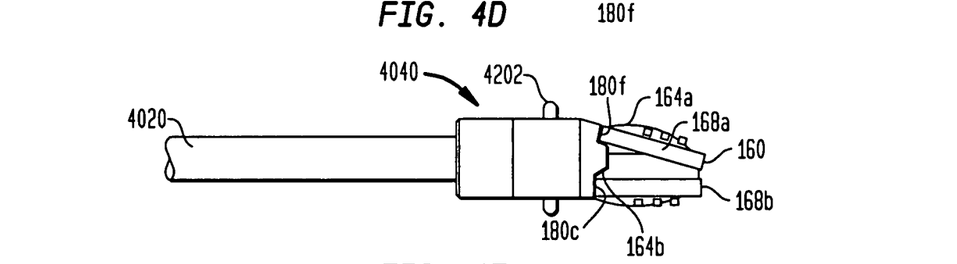
Figure 4E:
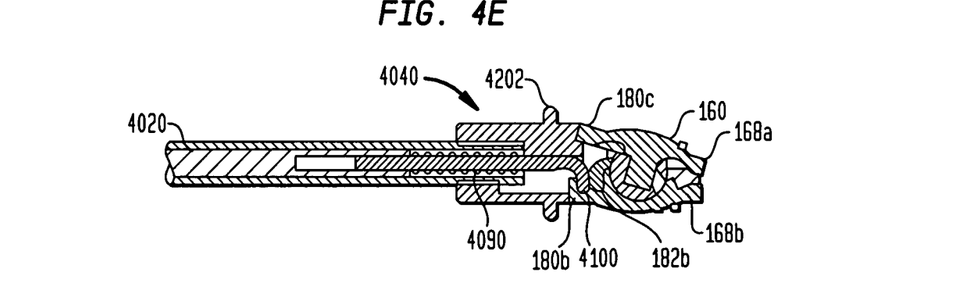

Referring now to FIGS. 2a-4e, FIGS. 2a-c side (FIG. 2a), perspective (FIG. 2b), and close-up perspective (FIG. 2c), and perspective (FIG. 4d) views of a wedge plate inserter/impactor of the present invention. FIGS. 3a-d show bottom (FIG. 3a), side (FIG. 3b), top (FIG. 3c), and side cutaway (FIG. 3d) views of a distal end of a wedge plate inserter/impactor of the present invention. FIGS. 4a-b show top (FIG. 4a) and side (FIG. 4b) views of a wedge plate inserter/impactor of the present invention holding an exemplary artificial intervertebral disc. FIGS. 4c-e show top (FIG. 4c), side (FIG. 4d), and side cutaway (FIG. 4e) views of a distal end of a wedge plate inserter/impactor of the present invention holding an exemplary artificial intervertebral disc.

It should be understood that the illustration and reference herein to the artificial intervertebral disc shown in FIGS. 1g-n of the '356 application is merely to show an example of one type of artificial intervertebral disc that is contemplated by, encompassed by, and suitable for use with, the present invention, and that such illustration and reference herein is not meant to limit the scope of the present invention or limit the uses of the present invention. Rather, any other artificial intervertebral disc (or any other orthopedic device) having suitable features for being used with the instrumentation and methods described herein are contemplated by the present invention. Indeed, the features suitable for manipulation (e.g., angled flat surfaces with adjacent holes and/or opposing notches, and/or inwardly facing baseplate surfaces) are encompassed by the present invention, regardless of to what orthopedic device they may be applied. Other exemplary suitable artificial intervertebral discs include, but are not limited to, the artificial intervertebral discs described in the '160 application with regard to FIGS. 8a-y, 9a-t, 10a-t, 11a-j, and 12a-o thereof and by the accompanying descriptions therefor (e.g., embodiments identified as the first, second, third, fourth, and fifth preferred embodiments of the fourth embodiment family, etc.). It should be noted that, as can be seen from FIGS. 1g-n of the '356 application, that the artificial intervertebral disc shown in FIGS. 1g-n of the '356 application has features similar to those of these other suitable artificial intervertebral discs of the '160 application, and it should be understood that such similar features are structurally and functionally as described in the '160 application. Such similar features include an inwardly facing surface of the upper baseplate, and a convex structure on the lower baseplate, the convex structure having an inwardly facing surface.

And, while the instrumentation described herein (e.g., the inserter/impactor) as well as the instrumentation described in the '356 application (e.g., the inserter/impactor described therein) will be discussed for use with the artificial intervertebral disc of FIGS. 1g-n of the '356 application, such discussions are merely by way of example and not intended to be limiting of their uses. Thus, it should be understood that the tools can be used with any of the artificial intervertebral discs disclosed in the '356 application or the '160 application, or any other artificial intervertebral disc having (or being modifiable or modified to have) suitable features therefor. Moreover, it is anticipated that the features of the artificial intervertebral disc (e.g., the angled flat surfaces and the inwardly facing baseplate surfaces, and accompanying holes) that are used by the tool discussed herein (or in the '356 application) to hold and/or manipulate these devices (certain features, it should be noted, were first shown and disclosed in the '160 application, the '127 application, and/or the '356 application) can be applied, individually or collectively or in various combinations, to other trials, spacers, artificial intervertebral discs or other orthopedic devices as stand-alone innovative features for enabling such trials, spacers, artificial intervertebral discs, or other orthopedic devices to be more efficiently and more effectively held and/or manipulated by the tools described herein (or in the '356 application) or by other tools having suitable features. In addition, it should be understood that the invention encompasses artificial intervertebral discs, spacers, trials (static or dynamic), and/or other orthopedic devices, that have one or more of the features disclosed herein (or in the '356 application), in any combination, and that the invention is therefore not limited to artificial intervertebral discs, spacers, trials, and/or other orthopedic devices having all of the features simultaneously.

Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs.

The inserter/impactor 4000 is provided primarily for holding, inserting, repositioning, removing, impacting, extracting, and otherwise manipulating an artificial intervertebral disc having features suitable for being manipulated by the inserter/impactor. (However, it can also be used to hold, insert, reposition, remove, impact, extract, and otherwise manipulate any other orthopedic device having suitable features therefor. For example, it should be understood that distraction of an intervertebral space can be accomplished in conjunction with a cooperating tool or spacer that can be gripped by the inserter/impactor.) Exemplary suitable artificial intervertebral discs include, but are not limited to, the artificial intervertebral disc 160 described herein and the artificial intervertebral discs described in the '160 application with regard to FIGS. 8*a-y*, 9*a-t*, 10*a-t*, 11*a-j*, and 12*a-o* thereof and by the accompanying descriptions therefor (e.g., embodiments identified as the first, second, third, fourth, and fifth preferred embodiments of the fourth embodiment family, etc.). Regarding the features suitable for being manipulated by the inserter/impactor 4000, such features include those discussed above as being suitable features on the disc 160, namely, an anteriorly facing flat surface on the second (e.g., lower) baseplate of the trial or disc, flanked by two anteriolaterally facing flat surfaces (one on each side of the anteriorly facing flat surface), and, to provide for holding of the trial or disc for an anterior insertion approach, a hole spaced from the anteriorly facing flat surface, the hole having a longitudinal axis parallel to the anteriorly facing flat surface. Further regarding the features suitable for being manipulated by the inserter/impactor, such features further include the inwardly facing surfaces of the baseplates of the disc.

More particularly, the inserter/impactor 4000 includes a shaft 4020 having a distal end 4040 that has angled flat surfaces 4200*a-c* corresponding to and fittable against angled flat surfaces of the artificial intervertebral disc (e.g., the surfaces 180*a-c* of the artificial intervertebral disc 160) to be implanted. The distal end 4040 has angled flat surfaces 4200*d-f* corresponding to and fittable against angled flat surfaces of the artificial intervertebral disc (e.g., the surfaces 180*d-f* of the artificial intervertebral disc 160) to be implanted. The distal end 4040 has a wedge-shaped extension 4042 including upper 4200*g* and lower 4200*h* wedge surfaces corresponding to and fittable against the inwardly facing surfaces of the artificial intervertebral disc (e.g., the lower surface 164*a* of the upper baseplate 168*a* of the disc 160, and the upper surface 164*b* of the lower baseplate 168*b* of the disc 160, respectively) to be implanted. For example, in an anterior approach for the disc 160 (as shown in FIGS. 4*a-e*), 180*a* and 180*d* facing 4200*a* and 4200*d*, 180*b* and 180*e* facing 4200*b* and 4200*e*, 180*c* and 180*f* facing 4200*c* and 4200*f*, and 164*a* facing 4200*g* and 164*b* facing 4200*h*.

The inserter/impactor 4000 holds the disc 160 in a preferred position with respect to the inserter/impactor 4000. (It should be understood that the surfaces of the wedge-shaped extension 4042 can be modified within the scope of the present invention to hold the disc 160 (or another orthopedic device) at positions other than those illustrated herein.) In the illustrated embodiment of the inserter/impactor 4000 in use with the disc 160, the preferred position is with the baseplates 168*a,b* of the disc 160 angle at 15 degrees of lordosis with respect to one another. More particularly, preferably, the upper and lower surfaces (e.g., 4200*g* and 4200*h*) of the wedge-shaped extension 4042 protrude from the distal end 4040 and are formed to hold the baseplates 168*a,b* such that they are angled at 15 degrees of lordosis with respect to one another. A surface (e.g., lower surface 4200*h*) of the wedge-shape extension 4042 that mates with an inwardly facing surface of a baseplate (e.g., the lower baseplate 168*b*) of a disc (e.g., 160) may be correspondingly shaped (e.g., curved or flat) for interaction or mating with the disc baseplate (e.g., the lower surface 4200*h* of the wedge-shaped extension as illustrated is curved to accommodate the surface of the shield of the disc). Preferably, the forward surface 4200*i* of the wedge-shaped extension 4042 has a concave curvature towards the shaft 4020 of the inserter/impactor 4000, also for accommodating the curvature of the surface of the shield of the disc.

Also preferably with regard to the preferred positioning, the wedge surfaces of the distal end 4040 protrude from a distance midway with respect to the top and bottom of the distal end 4040 and span (e.g., right to left or vice-versa) the entire distal face of the distal end 4040, and the surfaces 4200*d-f* above the wedge on the distal end 4040 are respectively perpendicular to the wedge's upper surface 4200*g* such that each is disposed in parallel with its respective corresponding surface of the disc 160 when the disc 160 is held by the inserter/impactor 4000 at the appropriate lordosis angle. (And, accordingly, are angled approximately 15 degrees with respect to the surfaces below the wedge 4200*a-c*.) Preferably, for an anterior approach, the wedge-shaped extension 4042 is designed and shaped to fit with its antero-lateral confronting surfaces (4200*d,f* and 4200*a,c*) tightly against the correspondingly antero-laterally facing surfaces (180*d,f* and 180*a,c*) of the disc 160, but such that its anterior confronting surfaces (4200*e* and 4200*b*) are slightly spaced from the anteriorly facing surfaces (180*d* and 180*b*) of the disc 160, when the disc is held by the inserter/impactor 4000. This is primarily to address manufacturing issues (in some cases, tolerances may not be adequately defined to ensure that all of those surfaces fit tightly against their corresponding surfaces), so that if there are manufacturing anomalies, any slight tolerance differences that may exist are nevertheless still adequate to ensure at least the tight fitting of the antero-lateral confronting surfaces, so that manipulation of the disc 160 is possible (e.g., in the manner of a wrench against an angled nut). This can be achieved, e.g., by designing the anterior confronting surfaces (4200*e* and 4200*b*) to each be slightly greater in length than the corresponding anteriorly facing surfaces (180*e* and 180*b*) of the disc baseplates, while still being angled with respect to the antero-lateral confronting surfaces (4200*d,f* and 4200*a,c*) at the same angle the antero-laterally facing surfaces (180*d,f* and 180*a,c*) of the disc baseplates are angled with respect to the anteriorly facing surfaces (180*e* and 180*b*) of the disc. The increased length of the anterior confronting surfaces on the wedge extension results in the slight clearance between the anteriorly facing surfaces (180*e* and 180*b*) of the disc and the corresponding anterior confronting surface (4200*e* and 4200*b*) of the wedged distal end, thereby ensuring that the disc will be fully seated against the antero-lateral confronting surfaces of the distal end despite possible manufacturing, material or other inevitable variations in tolerances of the artificial intervertebral disc or the inserter/impactor. As noted above, similar in this regard to the manner in which a wrench engages a nut, this fitting increases the mechanical advantage toward repositioning the disc in the intervertebral space. It should be noted, inasmuch as the inserter/impactor 4000 described herein can engage the disc from the antero-lateral angles as well, the anterior confronting surfaces (4200e and 4200b) should also be longer than the antero-laterally facing surfaces (180d,f and 180a,c) of the disc, so that a similar fitting occurs when the disc is held from the antero-lateral angles. Stated broadly, the primary confronting surfaces (e.g., the anterior confronting surfaces) of the inserter/impactor are preferably slightly longer than the primary confronted surfaces (e.g., anteriorly facing surfaces) of the disc for any given holding orientation.

Further, the inserter/impactor 4000 includes a holding pin 4080 that extends from the wedge 4042 along a longitudinal axis of the shaft 4020, the pin 4080 having a distal end 4100 that is bent downwardly. The holding pin 4080 is spring loaded (e.g., by a spring 4090) in a central channel of the shaft 4020, so that it is biased toward the shaft 4020 (preferably, the bent end 4100 of the pin 4080 prevents it from entering the central channel). The holding pin 4080 is restricted from upwardly lateral movement with respect to the distal end of the inserter/impactor by the presence of the wedge-shaped extensio 4042 of the distal end 4040 of the inserter/impactor 4000. More particularly, with any attempted upward movement of the holding pin 4080, the pin encounters the upper surface of the channel in which the pin 4080 travels, preventing any such upward movement. The holding pin 4080 is preferably heat treated (e.g., cold formed) to increase material quality (e.g., strength).

A flange 4110, mechanically connected to the pin 4080 and translating adjacent the shaft 4020, can be pushed distally to overcome the bias of the spring 4090 to space the pin 4080 away from the wedge 4042. (An alternative configuration is one in which the flange 4110 and the pin 4080 are formed from a single piece, rather than being mechanically connected.) In this extended position, the pin 4080 can be inserted in a hole (e.g., 182b) in the baseplate (e.g., 168b) of the artificial intervertebral disc (e.g., 160). Releasing the flange 4110 allows the spring 4090 to pull the pin 4080 back, causing the anteriorly facing surface 180b of the baseplate 168b to be held against the lower central flat surface 4200b of the inserter/impactor 4000 and the anterioloaterally facing flat surfaces 180a,c of the artificial intervertebral disc 160 to be held against the other corresponding flat surfaces 4200a,c of the inserter/impactor 4000. This can be further understood in light of the description of the manner in which the inserter/impactor of the '160 application functions to grip an orthopedic device, which is included in the '160 application and incorporated by reference herein. Simultaneously, the anteriorly facing surface 180e of the baseplate 168a is pulled against the upper central flat surface 4200e of the inserter/impactor 4000 and the anterioloaterally facing flat surfaces 180d,f of the artificial intervertebral disc 160 is pulled against the other corresponding flat surfaces 4200d,f of the inserter/impactor 4000. Additionally, the upper and lower wedge surfaces (4200g,h) interfere between the inwardly facing surfaces 164a,b of the disc baseplates, causing the baseplate to be angled at a 15 degree lordosis angle, with the lower surface 164a of the upper baseplate 168a held against the upper surface 4200g, and the upper surface of the shield being held against the lower surface 4200h, as best shown in FIGS. 4a-e.

A knob 4120, threaded on the shaft 4020, can be rotated about the longitudinal axis of the shaft 4020 to push the flange 4110 farther proximally, to pull the pin 4090 tighter and therefore lock its position (the interference of the threads of the knob-shaft interface prevents the knob 4120 from moving distally unless the knob 4120 is reverse rotated to effect that result) to more securely hold the baseplate 168b, and reverse rotated to unlock and loosen the pin 4080.

When the disc 160 is held in this manner, rotation of the disc 160 about a longitudinal axis (of the disc 160) relative to the inserter/impactor 4000 is prevented by interference of the corners of the disc's 160 flat surfaces (180a-c and 180d-f) and the corners of the inserter/impactor's 4000 flat surfaces (4200a-c and 4200d-f), similar to the manner in which a wrench holding a nut prevents rotation of the nut relative to the wrench. Further, the holding of the disc 160 in this manner allows for some repositioning of the disc 160 in the intervertebral space via rotation of the disc 160 in either direction about the longitudinal axis of the intervertebral space. Further when the disc is held in this manner, rotation of the disc about a lateral axis (of the disc 160) relative to the inserter/impactor 4000 is prevented by interference of the inwardly facing surface 164a of the first baseplate (e.g., upper baseplate) of the disc and the upper surface 4200g of the wedge on the distal end 4040, and by interference of the inwardly facing surface 164b of the second baseplate (e.g., lower baseplate) of the disc and the lower surface 4200h of the wedge on the distal end 4040. Accordingly, the holding of the disc in this manner allows for some repositioning of the disc in the intervertebral space via rotation of the disc in either direction about the longitudinal or latitudinal axis of the intervertebral space In some embodiments, when the artificial intervertebral disc 160 is held by the inserter/impactor 4000, the flat surfaces 180a-c are more closely confronted by the angled flat surfaces 4200a-c of the inserter/impactor 4000, compared with the flat surfaces 180d-f being less closely confronted by the angled flat surfaces 4200d-f of the inserter/impactor 4000. As such, the structure of the artificial intervertebral disc 160 having the flat surfaces 180d-f (e.g., the upper baseplate 168a) has slightly more rotation and angulation freedom relative to the inserter/impactor 4000 when being held, compared to the structure of the artificial intervertebral disc 160 having the flat surfaces 180a-c (e.g., the lower baseplate 168b). This permits the artificial intervertebral disc 160 to adjust to the intervertebral space (e.g., to the angulation of the adjacent vertebral endplates, defining the intervertebral space, relative to one another) as it is being inserted thereinto. That is, typically, the adjacent vertebral endplates will be lordotically angled with respect to one another as a result of the intervertebral space being prepared and distracted.

Preferably, in order to provide for a holding of the disc 160 for two additional (here, anteriolateral) insertion approaches, each disc 160 also includes two additional holes 182a and 182c, one (e.g., 182a) spaced apart from one of the anteriolaterally facing flat surfaces (e.g. 180a), and the other (e.g. 182c) spaced apart from the other of the anteriolaterally facing flat surfaces (e.g. 180c). Accordingly, operation of the inserter/impactor 4000 can fit the holding pin 4080 into either of these two additional holes 182a or 182c, and hold the associated anteriolaterally facing flat surface (the one associated with the hole into which the pin 4080 is fit) of the disc 160 against the flat surface of the inserter/impactor 4000 opposite the pin 4080. For example, in a first anteriolateral approach for the disc 160, 180a and 180d facing 4200b and 4200e, 180c and 180f not confronted, and 180b and 180e facing 4200c and 4200f, and in a second anteriolateral approach for the disc 160, 180b and 180e facing 4200a and 4200d, 180a and 180d not confronted, and 180c and 180f facing 4200b and 4200e. It should be understood that preferably, in order to facilitate these additional approaches, the angle separating the anteriorly facing flat surface of the disc 160 and one of the anteriolaterally facing flat surfaces of the disc 160 is equal to the angle separating the anteriorly facing flat surface and the other of the anteriolaterally facing flat surfaces. Preferably, the surfaces are angled with respect to one another at an angle of 33.4 degrees.

It should also be understood that the inclusion of additional adjacent angulated surfaces (or placing the angulated surfaces in other locations on the disc or other orthopedic device), and/or including corresponding holes adjacent to such surfaces, can provide the surgeon with additional approaches, e.g., other anteriolateral approaches, directly lateral approaches, posteriolateral approaches, and/or directly posterior approaches. For example, a trial or disc can have angled surfaces (and corresponding holes) along the entire perimeter of one or both of the baseplates, and thus enable the surgeon to engage the trial or disc from a number of angles, including anterior, posterior, lateral, anteriolateral, and posteriolateral angles.

The inserter/impactor 4000 further includes at a proximal end a cap 4140 for use as an impact surface if the disc 160 must be impacted further into the intervertebral space after insertion, or forcibly extracted from the intervertebral space. A mallet can be used to strike the cap 4140 (in a distal direction for impaction, or in a proximal direction (using the flange of the cap 4140) for extraction). It should be noted a striking of the cap 4140 will translate the striking force to the baseplates through the shaft 4020 and the flat surfaces, but will not damage the holding pin 4080 because the holding pin 4080 is spring loaded in the central channel and thus buffered from the striking force thereby. The distal end 4040 of the inserter/impactor 4000 further preferably includes at least one vertebral body stop 4202 that protrudes longitudinally with respect to the shaft 4020, from the surfaces of the distal end. The stops help prevent the inserter/impactor from being used to insert the disc (or other orthopedic device) too far into the intervertebral space.

Accordingly, the inserter/impactor 4000 can be used to grip the artificial intervertebral disc to be implanted, and hold the same during insertion and/or removal of the same, and is useful for a variety of surgical approach angles.

While there has been described and illustrated specific embodiments of instrumentation, it will be apparent to those skilled in the art that variations and modifications are possible without deviating from the broad spirit and principle of the invention. The invention, therefore, shall not be limited to the specific embodiments discussed herein.

What is claimed is:

1. An apparatus for manipulating an artificial intervertebral disc, the apparatus comprising:

a shaft having a bore including a longitudinal axis and a distal end having an extension, the extension including a confronting surface substantially perpendicular to the longitudinal axis of the shaft;

a holding pin having a straight portion and a downwardly bent distal end, the straight portion located partially internal the bore of the shaft along the longitudinal axis and being extendible and retractable along the longitudinal axis of the bore of the shaft, the downwardly bent distal end of the holding pin being perpendicular to the longitudinal axis of the bore of the shaft, the downwardly bent distal end of the holding pin adapted to be received in an engagement hole of said artificial intervertebral disc, wherein the engagement hole has a longitudinal axis perpendicular to the longitudinal axis of the bore of the shaft, and wherein the holding pin is in an extended position along the longitudinal axis of the bore of the shaft when the downwardly bent distal end of the holding pin is received in the engagement hole of said artificial intervertebral disc;

a spring coupled to the holding pin and located internal to at least a portion of the bore of the shaft, the spring configured to bias the straight portion of the holding pin further into the bore of the shaft; and a flange mechanically coupled to the holding pin, wherein exerting pressure on the flange in a distal direction overcomes the spring-load of the spring to space the holding pin at a distance from the distal end extension of the shaft, wherein the downwardly bent distal end of the holding pin is prevented from being retracted within the bore of the shaft under the bias of the spring as the downwardly bent distal end of the holding pin abuts the confronting surface of the distal end of the shaft, and wherein a lower surface of the distal end extension of the shaft prevents the holding pin from upward movement with respect to the shaft distal end.

2. The apparatus according to claim 1, wherein the artificial intervertebral disc comprises first and second articulating baseplates, and wherein the holding pin engages and disengages a corresponding engagement hole of the first baseplate.

3. The apparatus according to claim 1, the apparatus further comprising a knob coupled to the shaft, wherein rotation of the knob moves the flange such that the holding pin moves into the extended position, and wherein reverse rotation of the knob moves the flange such that the holding pin moves into a retracted position.

4. The apparatus according to claim 3, wherein the knob is threaded to the shaft, and interference between threads of the knob and threads of the shaft lock the holding pin in position.

* * * * *